US008977796B2

(12) United States Patent
Engelhardt et al.

(10) Patent No.: US 8,977,796 B2
(45) Date of Patent: *Mar. 10, 2015

(54) COMBINATION ELECTRONIC DEVICE DOCK AND DISSINFECTOR

(71) Applicant: Readydock, Inc., West Hartford, CT (US)

(72) Inventors: David G. Engelhardt, Canton, CT (US); William A. Saimond, Canton, CT (US)

(73) Assignee: Readydock, Inc., West Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/101,721

(22) Filed: Dec. 10, 2013

(65) Prior Publication Data

US 2014/0248179 A1 Sep. 4, 2014

Related U.S. Application Data

(63) Continuation of application No. 13/543,055, filed on Jul. 6, 2012, now Pat. No. 8,606,981, which is a continuation of application No. 12/849,301, filed on Aug. 3, 2010, now Pat. No. 8,296,493.

(60) Provisional application No. 61/231,084, filed on Aug. 4, 2009.

(51) Int. Cl.
| | | |
|---|---|---|
| *G01N 21/33* | (2006.01) | |
| *A61L 2/00* | (2006.01) | |
| *H02J 1/00* | (2006.01) | |
| *H04M 1/00* | (2006.01) | |
| *A61L 2/10* | (2006.01) | |
| *A61L 2/20* | (2006.01) | |
| *H02J 7/00* | (2006.01) | |

(52) U.S. Cl.
CPC ... *A61L 2/10* (2013.01); *A61L 2/20* (2013.01); *H02J 7/0044* (2013.01); *H02J 7/0029* (2013.01)
USPC .......... 710/303; 250/504 R; 250/365; 422/24; 379/452; 379/441; 455/575.1; 455/575.6

(58) Field of Classification Search
CPC .............. G01N 21/33; H02J 1/00; H02J 7/00; G21K 5/08
USPC .................. 710/303; 250/504 R, 365; 422/24; 379/452, 441; 455/575.1, 575.6
See application file for complete search history.

(56) References Cited

U.S. PATENT DOCUMENTS

| | | |
|---|---|---|
| 4,740,706 A | 4/1988 | Murdock, III |
| 4,903,222 A | 2/1990 | Carter et al. |

(Continued)

*Primary Examiner* — Nikita Wells
(74) *Attorney, Agent, or Firm* — McCarter & English, LLP

(57) ABSTRACT

Disclosed is a disinfecting docking station for at least one portable electronic device, such as a medical technician's tablet computer, that has at least one recharging connector. An enclosure is adapted to receive the at least one portable electronic device therein through an openable side that includes a selectively closable door. Each electronic device is exposed to a disinfecting wavelength of light, such as UV light, to disinfect the surface of the device. The enclosure includes supports that minimally contact each device so that the device will be substantially exposed to the UV light. A control circuit monitors the exposure time and level, and is programmable to activate the UV light based on pre-set criteria. The enclosures may be stacked and provide power and network connectivity to each device while docked therein.

20 Claims, 5 Drawing Sheets

(56) References Cited

U.S. PATENT DOCUMENTS

| | | |
|---|---|---|
| 5,195,183 A | 3/1993 | Miller et al. |
| 5,317,691 A | 5/1994 | Traeger |
| 5,461,717 A | 10/1995 | Notarianni et al. |
| 5,477,415 A | 12/1995 | Mitcham et al. |
| 5,487,877 A | 1/1996 | Choi |
| 5,687,387 A | 11/1997 | Endejan et al. |
| 5,826,042 A | 10/1998 | Kirkendoll |
| 6,606,243 B2 | 8/2003 | Kamimaki et al. |
| 7,209,038 B1 | 4/2007 | Deconinck et al. |
| 7,424,314 B2 | 9/2008 | Park |
| 7,791,044 B1 | 9/2010 | Taylor et al. |
| 7,798,159 B2 * | 9/2010 | Palfy et al. .................... 134/184 |
| 8,296,493 B1 * | 10/2012 | Engelhardt et al. ........... 710/303 |
| 8,606,981 B2 * | 12/2013 | Engelhardt et al. ........... 710/303 |
| 2002/0122743 A1 | 9/2002 | Huang |
| 2008/0119241 A1 | 5/2008 | Dorogusker et al. |
| 2010/0309454 A1 | 12/2010 | Zhang |

* cited by examiner

US 8,977,796 B2

COMBINATION ELECTRONIC DEVICE DOCK AND DISSINFECTOR

CROSS-REFERENCE TO RELATED APPLICATIONS

This patent application is a continuation of U.S. patent application Ser. No. 13/543,055, filed Jul. 6, 2012, which is a continuation of U.S. application Ser. No. 12/849,301, filed Aug. 3, 2010, now U.S. Pat. No. 8,296,493, which claims the benefit under 35 U.S.C. §119(e) of U.S. Provisional Patent Application No. 61/231,084, filed Aug. 4, 2009, all of which are hereby incorporated by reference in their entireties as part of the present disclosure.

FIELD OF THE INVENTION

This invention relates to the eradication of pathogens, and more particularly to a recharging and disinfecting docking station for portable electronic products.

BACKGROUND OF THE INVENTION

Medical environments, such as hospitals and doctors' offices, are known to contain a relatively high concentration of pathogens. As a result, it is desirable to reduce such pathogens wherever they exist in such environments. As a doctor makes his rounds from patient to patient in a hospital, for example, the objects the doctor carries are susceptible to contamination throughout the day.

One such object a doctor may routinely carry is a medical tablet computer, which a doctor may use to make notes on a patient file, write prescriptions, and the like. Such portable electronic devices frequently need to be recharged, yet currently there is no provision in recharging stations for such devices for disinfecting such devices.

Therefore, there is a need for a device that not only charges portable electronic devices, but that also concurrently disinfects such devices. Such a needed device would allow for the charging of multiple portable electronic devices, and would ensure disinfecting wavelengths of light reach substantially every surface of each portable electronic device therein. The present invention accomplishes these objectives.

SUMMARY OF THE INVENTION

The present device is a disinfecting docking station for at least one portable electronic device, such as a medical technician's tablet computer, that has at least one recharging connector. A substantially opaque enclosure is adapted to receive the at least one portable electronic device therein through at least one openable side. The enclosure further includes at least one door for selectively sealing the openable side. The enclosure may include reflective inner surfaces therein for reflecting disinfecting wavelengths of light.

A recharging means for recharging each of the at least one portable electronic device through the recharging connector thereof is adapted to transmit disinfecting wavelengths of light to the at least one portable electronic device. The recharging means preferably includes a backplane connector for electrically communicating with the recharging connector of the at least one portable electronic device. The back plane connector is connected with a power source and is preferably at least partially transparent to the disinfecting wavelengths of light and capable of transmitting such light to substantially all of the surfaces of the recharging connector.

At least one means of supporting each of the at least one portable electronic device is included, each means of supporting adapted to transmit the disinfecting wavelengths of light to the at least one portable electronic device. Preferably each means of supporting each include at least one shelf surface, each of which is substantially transparent to the disinfecting wavelengths of light. Each shelf surface may be comprised of a relatively small surface area where actually contacting the portable electronic device.

At least one disinfecting means, each adapted for producing the disinfecting wavelengths of light only when the door is in a closed position, is included. A control circuit may be further included and electrically connected with the power source, a user interface disposed on an outside surface of the enclosure, a switch for detecting when the door is in the closed position, and the ultraviolet light source. Such a control circuit includes a timer for activating the ultraviolet light source only when the switch indicates that the door is in the closed position and only for a predetermined period of time once activated by the user interface.

In use, with at least one of the portable electronic devices supported by the means of supporting within the enclosure and the door in the closed position, the means for disinfecting may be activated to produce the disinfecting wavelengths of light, illuminating substantially each surface of each of the portable electronic devices for a predetermined period of time.

The present invention is a device that charges and concurrently disinfects portable electronic devices. The present device allows for the charging of multiple portable electronic devices, and ensures disinfecting wavelengths of light reach substantially every surface of each portable electronic device therein. Other features and advantages of the present invention will become apparent from the following more detailed description, taken in conjunction with the accompanying drawings, which illustrate, by way of example, the principles of the invention.

DETAILED DESCRIPTION OF THE INVENTION

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Figure 1:
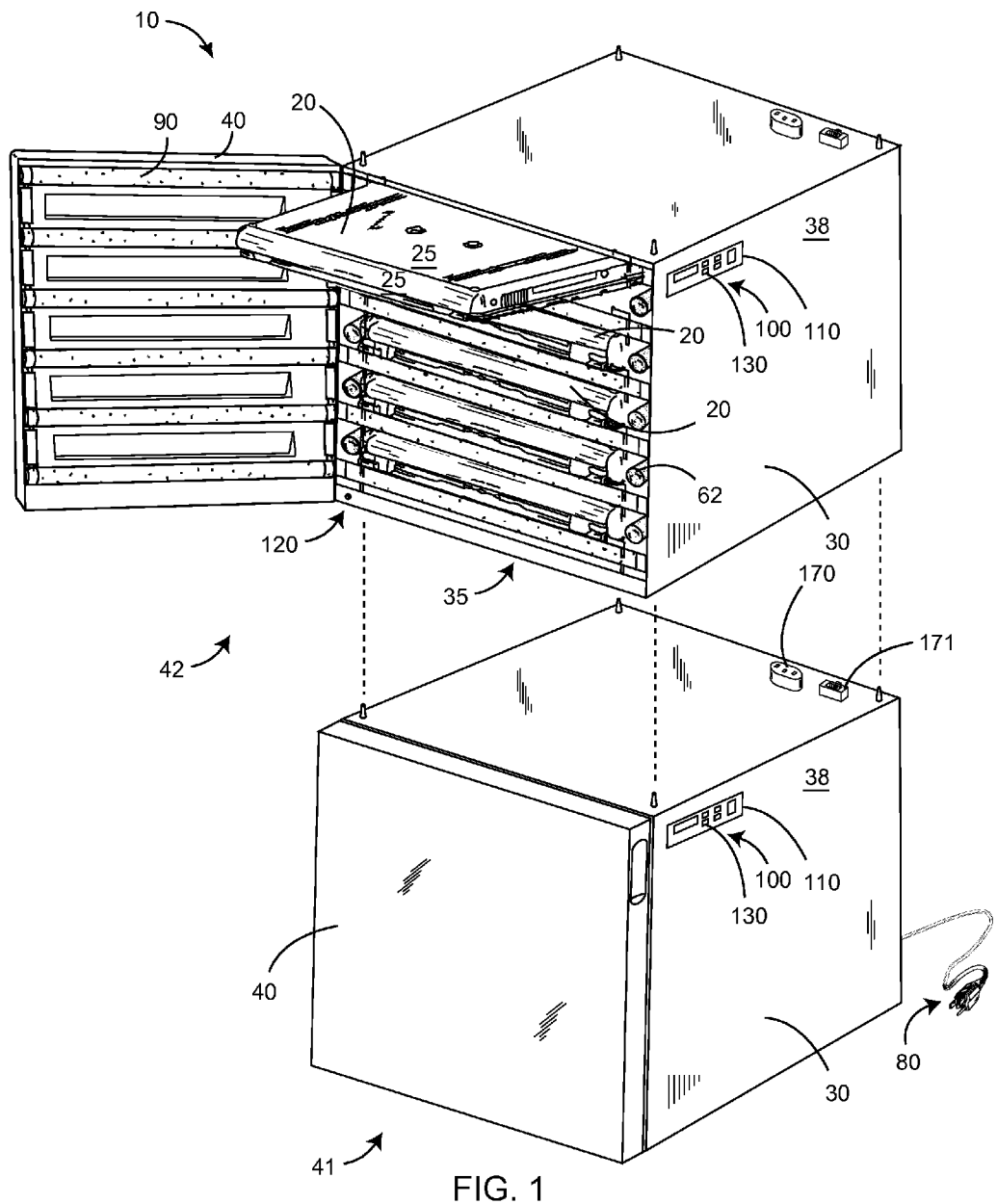
FIG. 1 is a perspective view of the invention, illustrate a stack of docking stations of the invention with daisy-chain power and network connectors.
Figure 2:
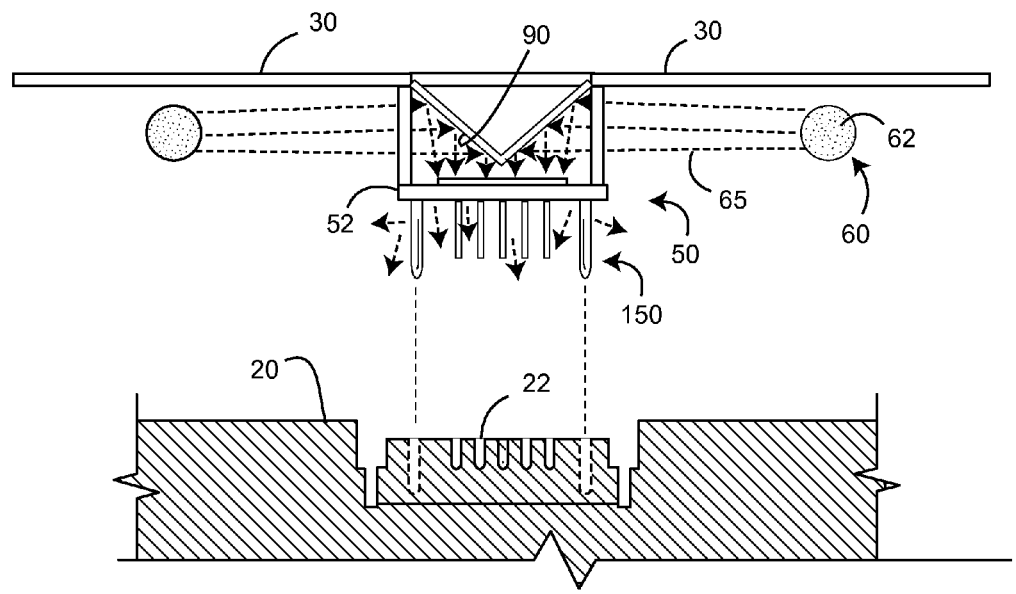
FIG. 2 is a top view of a recharging means thereof.

FIGS. 1 and 2 illustrate a disinfecting docking station 10 for at least one portable electronic device 20, such as a medical technician's tablet computer, that has at least one recharging connector 22 and may include various crevices 26 therein for air ducting ports, alternate connectors, door or compartment actuators, or the like. While the illustrations herein show the invention as used with tablet computers, any portable electronic device may be used, such as portable phones, music players, electronic book readers, or other electronic devices used in environments where reduction of pathogens is desirable.

A substantially opaque enclosure 30 is adapted to receive the at least one portable electronic device 20 therein through at least one openable side 35. The enclosure 30 further includes at least one door 40 for selectively sealing the openable side 35 between a closed position 41 and an open position 42 (FIG. 1). The door 40 is preferably connected with the enclosure 30 through a suitable hinge arrangement. The enclosure 30 may include reflective inner surfaces 90 therein for reflecting disinfecting wavelengths of light 65 about the enclosure 30. The enclosure 30 is made of any suitably rigid, strong, opaque material, such as metal, plastic, or the like.

A recharging means 50 for recharging each of the at least one portable electronic device 20 through the recharging connector 22 thereof is adapted in one embodiment to transmit disinfecting wavelengths of light 65 to the at least one portable electronic device 20. The recharging means 50 preferably includes a backplane connector 52 for electrically communicating with the recharging connector 22 of the at least one portable electronic device. The back plane connector 52 is connected with a power source 80 and is preferably at least partially transparent to the disinfecting wavelengths of light 65 and capable of transmitting such light 65 to substantially all of the surfaces of the recharging connector 22. In one embodiment, the backplane connector 52 includes a plurality of elongated, relatively thin electrical pins 150 (FIG. 2), around which the disinfecting wavelengths of light 65 may travel so as to fully expose the recharging connector 22. The backplane connector 52 may be included at a rear side of the enclosure 30, as illustrated, or elsewhere within the enclosure 30 as necessary based on the type of portable electronic devices used therewith and the location of its recharging connector 22.

At least one means of supporting 70 each of the at least one portable electronic device 20 is included, each means of supporting 70 adapted to transmit the disinfecting wavelengths of light 65 to the at least one portable electronic device 20. Preferably each means of supporting 70 includes at least one shelf surface 72, each of which is substantially transparent to the disinfecting wavelengths of light 65. In one embodiment, each means of supporting 70 includes at least one reflective surface 90 for reflecting a portion of the disinfecting wavelengths of light 65 into a crevice 26 of one of the at least one portable electronic device 20, as determined by the particular portable electronic device 20 used with the docking station 10. Such a crevice 26 may be, for example, an inset connector, a stylus or pen cavity, an inset screw access aperture, or the like. Each shelf surface 72 may be comprised of a relatively small surface area where actually contacting the portable electronic device 20, and may include small prongs, rollers (not shown) or other means having a small contact area with the electronic device 20. As such, 99% or greater of the surface 25 of each portable electronic device 20 may be exposed to the disinfecting wavelengths of light 65.

Alternately, each means of supporting 70 may be opaque and include support pins (not shown) that alternately extend and retract, such that, where alternately supported, each portable electronic device 20 is exposed to the disinfecting wavelengths of light 65 in an alternating fashion.

Figure 7:
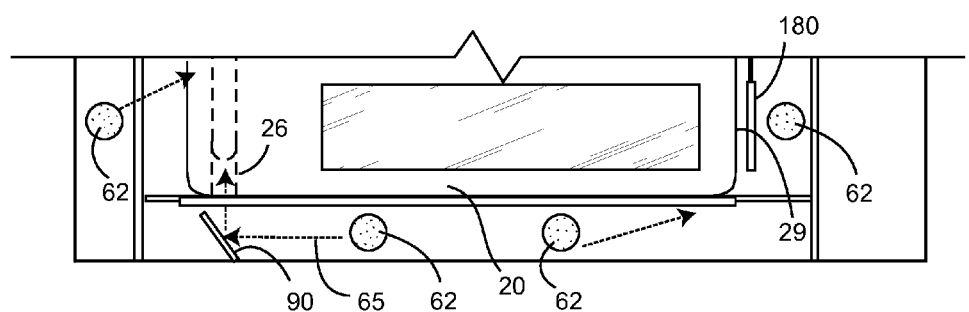
FIG. 7 is a partial top view of the invention.

At least one disinfecting means 60, each adapted for producing the disinfecting wavelengths of light 65 only when the door is in the closed position 42, is included. Preferably each disinfecting means 60 includes an ultraviolet light source 62, such as an ultraviolet light bulb. The enclosure 30 may further include a plurality of ultraviolet light filters 180 (FIG. 7) fixed within the enclosure 30 to block at least some of the ultraviolet light 65 from sensitive areas 29 of the portable electronic device 20, such as photocells or camera elements thereof, for example.

A control circuit 100 (FIGS. 1 & 3) may be further included and electrically connected with the power source 80, a user interface 110 disposed on an outside surface 38 of the enclosure 30, a switch 120 for detecting when the door 40 is in the closed position, and the ultraviolet light source 62. Such a control circuit 100 includes a timer 130 for activating the ultraviolet light source 62 only when the switch 120 indicates that the door 40 is in the closed position and only for a predetermined period of time once activated by the user interface 110. The user interface 110 and control circuit 100 may provide options for delivering varying durations or intensities of the disinfecting wavelengths of light 65, based on selections made at the user interface 110. For example, overnight disinfection of each portable electronic device 20 may include longer durations or stronger intensities of the disinfecting wavelengths of light 65 than disinfection between patient encounters. Further, the control circuit 100 may include provisions for illuminating a portion of the total number of ultraviolet light sources 62 within the enclosure 30, based on the number of portable electronic devices 20 contained therein.

In use, with at least one of the portable electronic devices 20 supported by the means of supporting 70 within the enclosure 30 and the door 40 in the closed position 41, the means for disinfecting 60 may be activated to produce the disinfecting wavelengths of light 65, illuminating substantially each surface 25 of each of the portable electronic devices for a predetermined period of time.

In one embodiment of the invention, each means for recharging 50 may be a retractable connector (not shown), such that after the predetermined period of time has elapsed and the means for disinfecting 60 has been deactivated by the control circuit 100, such a retractable connector may extend to engage the recharging connector 22 of the portable electronic device 20, the recharging connector 22 having been thoroughly disinfected by the disinfecting wavelengths of light 65 while previously disengaged from the means for recharging 50. In such an embodiment, the backplane connector 52 includes a motorized arrangement (not shown) for engaging the recharging connector 22, the motorized arrangement controlled by the control circuit 100. It is understood that the term "recharging connector" used herein may also refer to other types of connectors, such as network connectors, interface connectors, VGA connectors, and the like.

Figure 4:
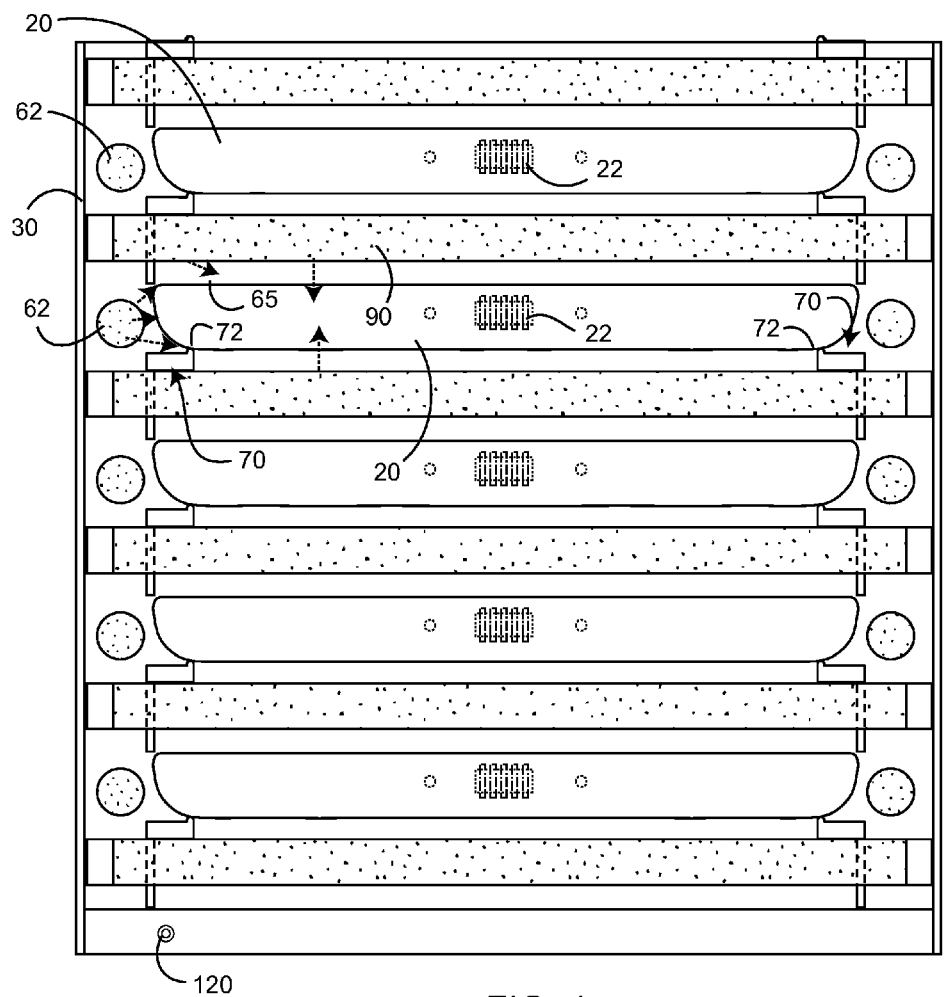
FIG. 4 is a front diagram of one embodiment of the invention wherein ultraviolet light sources of the invention are oriented in a coplanar configuration with a plurality of portable electronic devices stored within an enclosure of the invention.
Figure 5:
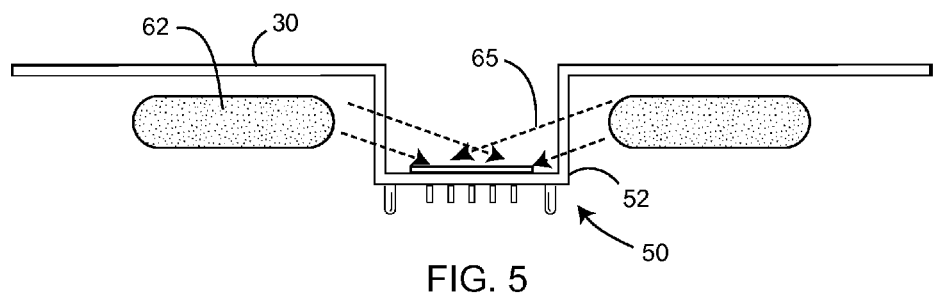
FIG. 5 is a top view of an alternate means for recharging each portable electronic device.

The control circuit 100 may allow for varying exposure time and intensity of the disinfecting wavelengths of light 65 depending on selections made at the user interface 110. For example, a "double" disinfecting dose of the disinfecting wavelengths of light 65 may be selected on the user interface 110, which may double the exposure time of each portable electronic device 20 to the disinfecting wavelengths of light 65, for example. Further, in the case where the enclosure 30 holds a plurality of the portable electronic devices 20, any particular device 20 may be selected for exposure to the disinfecting wavelengths of light 65 at the user interface 110. For example, "bay 3" (not shown) may be selected, whereupon the control circuit only activates the ultraviolet light sources 62 associated with that particular location within the enclosure 30. A suitable embodiment for such functionality is illustrated in FIG. 4.

Figure 3:
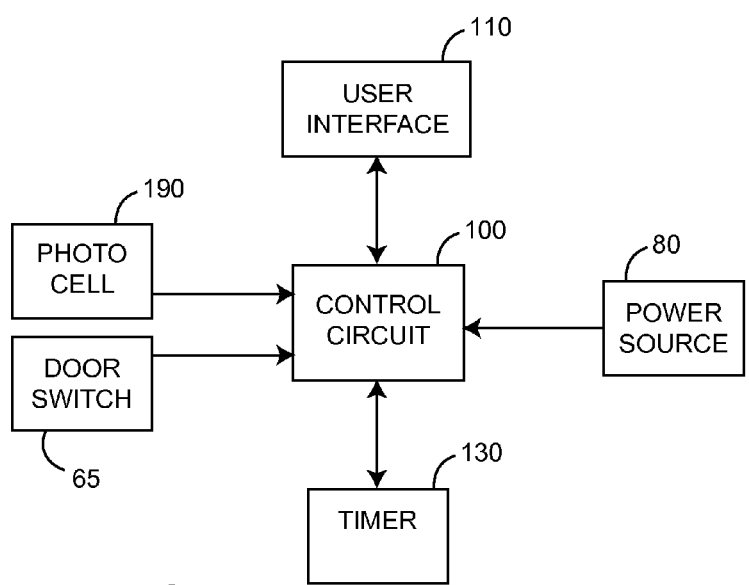
FIG. 3 is a diagram of various components of a control circuit of the invention.

In one embodiment, the control circuit 100 is further connected to at least one photocell 190 sensitive to ultraviolet light, such that the control circuit 100 may activate the ultraviolet light source 62 only for a duration sufficient to provide a predetermined dose, or number of lumens, for example, to each portable electronic device 20, as determined by the at least one photocell 190 and the control circuit 100 (FIG. 3).

Figure 8:
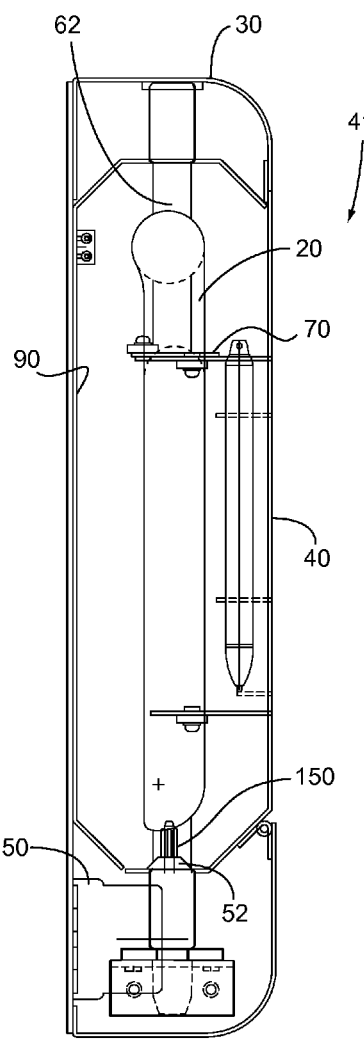
FIG. 8 is a partially cut-away side elevational view of an alternate embodiment of the invention in a closed position.
Figure 9:
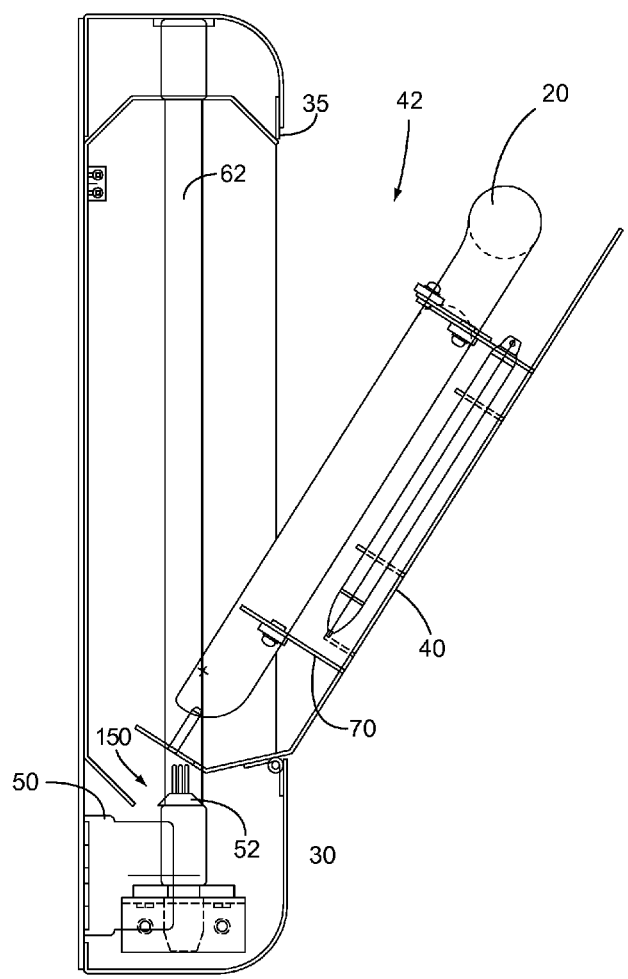
FIG. 9 is a partially cut-away side elevational view of the embodiment of FIG. 8 in an open position.

In one embodiment, each door 40 includes the means of supporting 70 and is pivotally attached with the enclosure 30 at a lower end 43 thereof (FIGS. 8 and 9). In such an embodiment, the enclosure 30 may be adapted to hold only a single portable electronic device 20, or the enclosure 30 may be equipped with a plurality of such doors 40 to hold a plurality of single portable electronic devices 20.

Figure 6:
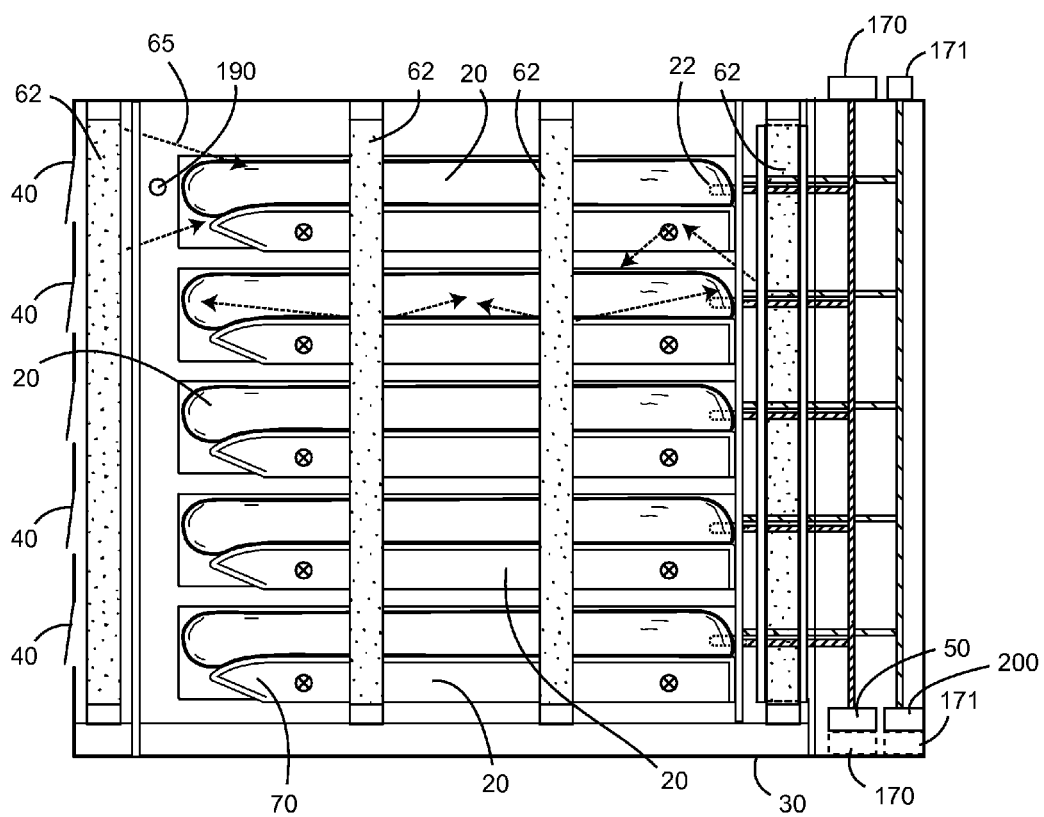
FIG. 6 is a side view of an alternate embodiment of the invention, wherein the ultraviolet light sources of the invention are oriented substantially perpendicular to the plurality of portable electronic devices stored within the enclosure.

Preferably the power source 80 of the enclosure 30 includes a daisy chain connector 170 fixed with the enclosure 30 such that a plurality of enclosures 30 can be stacked (FIGS. 1 and 6), each enclosure 30 connecting with the daisy chain connector 170 of its next adjacent enclosure 30. As such, a single power source 80 may be included and connected to each enclosure 30 in stack of such enclosures 30 through each enclosure's daisy chain connector 170. It is understood that the power source may be an A/C line voltage source, or a low-voltage D/C source.

In a similar manner, each enclosure 30 may further include a network switch means 200 for providing network connectivity to each of the portable electronic device 20 stored therein. A network daisy chain connector 171 may be included for electrically connecting each network switch means 200 of each enclosure 30 in a stack of such enclosures 30, whereby only one network connection is required for the stack of enclosures 30. For portable electronic devices 20 that include wireless network capability, such as through WiFi or the like, a radio frequency refractor (not shown) may be included within the enclosure 30 so as to allow such wireless radio signals to pass substantially unimpeded through the enclosure 30.

While a particular form of the invention has been illustrated and described, it will be apparent that various modifications can be made without departing from the spirit and scope of the invention. For example, the particular shape of the enclosure 30, and the number of portable electronic devices 20 illustrated in the drawings, may be altered considerably as desired. Accordingly, it is not intended that the invention be limited, except as by the appended claims.

The teachings provided herein can be applied to other systems, not necessarily the system described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the system may vary considerably in its implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A disinfecting docking station for at least one portable electronic device having at least one recharging connector, comprising:
   a substantially opaque enclosure adapted to receive at least one portable electronic device therein through at least one openable side, the enclosure further including means for selectively sealing the at least one openable side;
   means for recharging the at least one portable electronic device through a recharging connector thereof;
   at least one means for supporting the at least one portable electronic device; and
   at least one ultraviolet light source adapted to produce disinfecting wavelengths of light only when the means for selectively sealing is in a closed position;
   whereby, with the at least one portable electronic device supported by the at least one means for supporting within the enclosure and with the means for selectively sealing in the closed position, the at least one ultraviolet light source is activatable to produce disinfecting wavelengths of light, illuminating substantially each surface of the at least one portable electronic device for a predetermined period of time.

2. The disinfecting docking station of claim 1, wherein the means for recharging includes a connector adapted to electrically communicate with the recharging connector of the at least one portable electronic device, the connector being connected with a power source.

3. The disinfecting docking station of claim 1, wherein the at least one means for supporting includes at least one shelf surface substantially non-obstructive to the disinfecting wavelengths of light.

4. The disinfecting docking station of claim 1, wherein the at least one means for supporting further includes at least one reflective surface adapted to reflect at least a portion of the disinfecting wavelengths of light into a crevice of the at least one portable electronic device.

5. The disinfecting docking station of claim 1, further including a control circuit electrically connected with a power source, a user interface disposed on an outside surface of the enclosure, a switch for detecting when the means for selectively sealing is in the closed position, and adapted to activate the ultraviolet light source, the control circuit including a timer, adapted to activate the ultraviolet light source for a predetermined period of time upon activation by the user interface, only when the switch indicates that the means for selectively sealing is in the closed position.

6. The disinfecting docking station of claim 5, wherein the control circuit is adapted to illuminate the at least one portable electronic device with the disinfecting wavelengths of light according to selections made at the user interface.

7. The disinfecting docking station of claim 1, wherein the means for selectively sealing includes the at least one means for supporting.

8. The disinfecting docking station of claim 1, further comprising a daisy chain connector fixed with the enclosure such that a plurality of enclosures can be stacked, each enclosure connecting with the daisy chain connector of an adjacent enclosure.

9. A disinfecting docking station for at least one portable electronic device having at least one recharging connector, comprising:
   a substantially opaque enclosure adapted to receive at least one portable electronic device therein through at least one openable side, the enclosure further including at least one door for selectively sealing the at least one openable side;
   at least one connector adapted to electrically communicate with the at least one portable electronic device through the recharging connector thereof;
   at least one shelf surface adapted to at least partially support the at least one portable electronic device; and
   at least one ultraviolet light source adapted to produce disinfecting wavelengths of light only when the at least one door is in a closed position;
   whereby, with the at least one portable electronic device supported by the at least one shelf surface within the enclosure, and the at least one door in the closed position, the at least one ultraviolet light source is activatable to produce the disinfecting wavelengths of light, illuminating substantially each surface of the at least one portable electronic device for a predetermined period of time.

10. The disinfecting docking station of claim 9, wherein the at least one shelf surface further includes at least one reflective surface adapted to reflect at least a portion of the disinfecting wavelengths of light into a crevice of the at least one portable electronic device.

11. The disinfecting docking station of claim 9, wherein the at least one door includes the at least one shelf surface, and is pivotably attached with the enclosure at an end thereof.

12. The disinfecting docking station of claim 9, further including a network switch adapted to provide network connectivity to the at least one portable electronic device.

13. The disinfecting docking station of claim 9, wherein the at least one shelf surface is adapted to substantially permit transmission of the disinfecting wavelengths of light therethrough and, in turn, to the at least one portable electronic device.

14. A method comprising the following steps:
   receiving at least one portable electronic device having at least one recharging connector within a disinfecting docking station comprising a substantially opaque enclosure, at least one connector adapted to electrically communicate with the at least one portable electronic device through the recharging connector thereof;
   illuminating substantially each surface of the at least one portable electronic device within the docking station with disinfecting wavelengths of light, and, in turn, disinfecting the at least one portable device; and
   recharging the at least one portable electronic device via the at least one connector.

15. A method as defined in claim 14, wherein the at least one connector is connected to a power source and the receiving step further comprises connecting the at least one recharging connector to said at least one connector.

16. A method as defined in claim 14, wherein the connector is at least partially transparent to the disinfecting wavelengths of light, and the illuminating step includes transmitting at least some of the disinfecting wavelengths of light through the connector and to substantially all surfaces of the at least one recharging connector.

17. A method as defined in claim 14, wherein the enclosure includes at least one openable side and at least one door for selectively sealing the at least one openable side, and the receiving step comprises inserting the at least one portable electronic device within the enclosure, and moving the at least one door into a closed position, sealingly closing the enclosure.

18. A method as defined in claim 17, performing the illuminating step when the at least one door is in the closed position.

19. A method as defined in claim 14, wherein the illuminating step comprises producing the disinfecting wavelengths of light with an ultraviolet light source, and illuminating substantially each surface for a predetermined period of time.

20. A method as defined in claim 14, wherein the docking station further comprises at least one shelf surface substantially transparent to the disinfecting wavelengths of light, the receiving step includes supporting the at least one portable electronic device with the at least one shelf surface, and the illuminating step includes substantially transmitting the disinfecting wavelengths of light through the at least one shelf surface and, in turn, substantially illuminating a surface of the at least one portable electronic device contacting the at least one shelf surface.

\* \* \* \* \*